United States Patent
Wernimont et al.

(10) Patent No.: US 11,950,571 B2
(45) Date of Patent: Apr. 9, 2024

(54) SYSTEM AND METHOD FOR ASSOCIATING A SIGNATURE OF AN ANIMAL MOVEMENT AND AN ANIMAL ACTIVITY

(71) Applicant: Hill's Pet Nutrition, Inc., Topeka, KS (US)

(72) Inventors: Susan Wernimont, Lawrence, KS (US); Robin Thompson, Newcastle upon Tyne (GB)

(73) Assignee: Hills Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 17/389,646

(22) Filed: Jul. 30, 2021

(65) Prior Publication Data
US 2022/0104464 A1   Apr. 7, 2022

Related U.S. Application Data

(60) Provisional application No. 63/086,247, filed on Oct. 1, 2020.

(51) Int. Cl.
*A01K 29/00* (2006.01)
*A61B 5/00* (2006.01)
(Continued)

(52) U.S. Cl.
CPC .......... *A01K 29/005* (2013.01); *A61B 5/1118* (2013.01); *A61B 5/7267* (2013.01);
(Continued)

(58) Field of Classification Search
CPC ... A01K 29/005; A61B 5/1118; A61B 5/7267; A61B 5/7282; A61B 2503/40; G01P 13/00; G06N 20/00; H04Q 9/00; H04Q 2209/40
See application file for complete search history.

(56) References Cited

U.S. PATENT DOCUMENTS 7,263,953 B2   9/2007   Sundararajan
7,434,541 B2   10/2008   Kates
(Continued)

FOREIGN PATENT DOCUMENTS

AU   2020102206   10/2020
CN   104871997   9/2015
(Continued)

OTHER PUBLICATIONS

FitBark 2 Dog Activity Monitor | Health & Fitness Tracker for Dogs | Waterproof, Small & Leightweight (10 g) | Not a GPS Tracker, Amazon.com, https://www.amazon.com/FitBark-Dog-Activity-Monitor-Black/dp/B077MDJYKQ, retrieved Oct. 1, 2020, pp. 1-4.
(Continued)

*Primary Examiner* — Amine Benlagsir

(57) ABSTRACT

A system, apparatus, and/or method of identifying an activity of an animal. The activity may include the animal drinking, eating, urination, or defecating. Motion data of a first animal may be received, for example, via a sensor. Predetermined signatures of one or more second animals may be received. The predetermined signatures of the one or more second animals may be associated with one or more activities of the one or more second animals. A signature of an activity of the first animal may be determined based on the motion data of the first animal. Based on the signature of the activity of the first animal and the predetermined signatures of the second animal, the activity of the first animal may be identified. The identified activity of the first animal may be displayed via a display device.

14 Claims, 8 Drawing Sheets

(51) Int. Cl.
*A61B 5/11* (2006.01)
*G01P 13/00* (2006.01)
*G06N 20/00* (2019.01)
*H04Q 9/00* (2006.01)

(52) U.S. Cl.
CPC ............ *A61B 5/7282* (2013.01); *G01P 13/00* (2013.01); *G06N 20/00* (2019.01); *H04Q 9/00* (2013.01); *A61B 2503/40* (2013.01); *H04Q 2209/40* (2013.01)

(56) References Cited

U.S. PATENT DOCUMENTS

| | | | |
|---|---|---|---|
| 7,616,124 | B2 | 11/2009 | Paessel et al. |
| 7,633,397 | B2 | 12/2009 | Dugan |
| 7,914,468 | B2 | 3/2011 | Shalon et al. |
| 9,055,733 | B2 | 6/2015 | Jones, II |
| 9,220,444 | B2 | 12/2015 | Russell |
| 9,226,692 | B2 | 1/2016 | Haas |
| 9,420,766 | B2 | 8/2016 | Triener |
| 9,572,647 | B2 | 2/2017 | Couse et al. |
| 9,717,216 | B1 | 8/2017 | Schlachta et al. |
| 9,788,232 | B2 | 10/2017 | Goldfain |
| 9,823,138 | B2 | 11/2017 | Zakharov et al. |
| 9,872,481 | B2 | 1/2018 | Goldfain |
| 10,091,972 | B1 | 10/2018 | Jensen et al. |
| 10,149,617 | B2 | 12/2018 | Couse |
| 10,154,655 | B2 | 12/2018 | Schab et al. |
| 10,314,292 | B2 | 6/2019 | Thorne |
| 10,463,023 | B2 | 11/2019 | Perz-Camargo et al. |
| 10,492,473 | B2 | 12/2019 | Menkes et al. |
| 10,716,492 | B2 | 7/2020 | Filipowicz |
| 10,761,107 | B2 | 9/2020 | Gyongy et al. |
| 10,785,957 | B2 | 9/2020 | Weinrauch et al. |
| 10,986,817 | B2 | 4/2021 | Singh et al. |
| 11,229,361 | B2 | 1/2022 | Coen et al. |
| 2002/0010390 | A1 | 1/2002 | Guice et al. |
| 2005/0197546 | A1 | 9/2005 | Mardiks et al. |
| 2007/0000216 | A1 | 1/2007 | Kater et al. |
| 2007/0021678 | A1 | 1/2007 | Beck et al. |
| 2009/0076346 | A1 | 3/2009 | James et al. |
| 2010/0218733 | A1* | 9/2010 | Jordan .................. A01G 25/16 119/720 |
| 2010/0321189 | A1* | 12/2010 | Gibson ................ A01K 29/005 340/573.3 |
| 2011/0125063 | A1 | 5/2011 | Shalon et al. |
| 2011/0169610 | A1 | 7/2011 | Geissler et al. |
| 2012/0143019 | A1 | 6/2012 | Russell |
| 2012/0274442 | A1 | 11/2012 | Mottram |
| 2014/0267299 | A1 | 9/2014 | Couse |
| 2014/0331942 | A1 | 11/2014 | Sarazyn |
| 2015/0181840 | A1 | 7/2015 | Tupin, Jr. et al. |
| 2016/0012748 | A1 | 1/2016 | Donavon |
| 2016/0042038 | A1* | 2/2016 | Schumacher ........ A01K 27/009 707/722 |
| 2016/0165853 | A1 | 6/2016 | Goldfain |
| 2016/0178392 | A1 | 6/2016 | Goldfain |
| 2016/0262356 | A1 | 9/2016 | Perez-Camargo et al. |
| 2016/0310012 | A1 | 10/2016 | Mankowski |
| 2017/0064926 | A1 | 3/2017 | Gutierrez |
| 2017/0105389 | A1 | 4/2017 | Sanchez |
| 2017/0231533 | A1 | 8/2017 | Qu et al. |
| 2018/0028095 | A1 | 2/2018 | Yamamoto |
| 2018/0084755 | A1* | 3/2018 | Hirschl ................ A01K 11/006 |
| 2019/0069518 | A1 | 3/2019 | Falbaum |
| 2019/0183092 | A1 | 6/2019 | Couse et al. |
| 2020/0060545 | A1 | 2/2020 | Maher et al. |
| 2020/0068853 | A1 | 3/2020 | Radovcic |
| 2020/0205381 | A1 | 7/2020 | Wernimont et al. |
| 2020/0236901 | A1 | 7/2020 | Trottier et al. |
| 2020/0253165 | A1* | 8/2020 | Luciew .................. A61F 13/82 |
| 2021/0065277 | A1 | 3/2021 | Bramson et al. |
| 2022/0087229 | A1 | 3/2022 | Wernimont et al. |
| 2022/0104464 | A1 | 4/2022 | Wernimont et al. |
| 2023/0141529 | A1 | 5/2023 | Wernimont et al. |
| 2023/0145392 | A1 | 5/2023 | Wernimont et al. |
| 2023/0147909 | A1 | 5/2023 | Wernimont et al. |

FOREIGN PATENT DOCUMENTS

| | | |
|---|---|---|
| CN | 109964846 | 7/2019 |
| CN | 210746676 | 6/2020 |
| CN | 112401888 | 2/2021 |
| EP | 3264299 | 1/2018 |
| EP | 3586618 | 1/2020 |
| GB | 2492110 | 12/2012 |
| GB | 2554636 | 4/2018 |
| JP | 4209294 | 1/2009 |
| JP | 2018-198553 | 12/2018 |
| KR | 102422186 | 7/2022 |
| WO | 2005/122755 | 12/2005 |
| WO | 2015/069037 | 5/2015 |
| WO | 2016/029138 | 2/2016 |
| WO | 2016/061529 | 4/2016 |
| WO | 2019/175115 | 9/2019 |
| WO | 2019/178222 | 9/2019 |
| WO | 2022/066282 | 3/2022 |
| WO | 2022/072049 | 4/2022 |
| WO | 2023/086315 | 5/2023 |

OTHER PUBLICATIONS

Hansen, B. D. et al., Evaluation of an accelerometer for at-home monitoring of spontaneous activity in dogs, (Jun. 2007) American Journal of Veterinary Research, ResearchGate, https://www.researchgate.net/publication/6358541_Evaluation_of_an_accelerometer_for_at-home_monitoring_of_spontaneous_activity_in_dogs, retrieved Oct. 1, 2020, pp. 1-8.

Link AKC Smart Dog Collar with GPS Tracker & Activity Monitor (Leather or Sport), Amazon.com, https://www.amazon.com/LINK-AKC-Smart-Dog-Collar/dp/B01MFG7ELX, retrieved Oct. 1, 2020, pp. 1-9.

PetPace Smart Collar with 12 Months Pet Plus Monitoring, Amazon.com, https://www.amazon.com/PetPace-Smart-Collar-Medium/dp/B01N1A2WKL, retrieved Oct. 1, 2020, pp. 1-7.

Whistle 3 GPS Pet Tracker Activity Monitor Grey: Pet Supplies, Whistle Go & Go Explore—The Ultimate Health + Location Tracker for Pets, Amazon.com, https://www.amazon.com/Whistle-GPS-Track-Activity-Monitor/dp/B01N7MWKWY, retrieved Oct. 1, 2020, pp. 1-7.

International Search Report and the Written Opinion of the International Searching Authority issued in International Application PCT/US2021/043879 dated Nov. 9, 2021, pp. 1-10.

Belk, Russell W., "Metaphoric Relationships with Pets", The White Horse Press Cambridge UK, 1996, pp. 121-145 (25 pages).

Belshaw, et al., "Slower, shorter, sadder: a qualitative study exploring how dog walks change when the canine participant develops osteoarthritis",BMC Veterinary Research, 2020, pp. 1-8.

Bentopal,"Interactive Dog Toy Wicked Ball for Indoor Cats/Dogs with Motion Activated/USB Rechargeable",https://www.amazon.com/BENTOPAL-Interactive-Wicked-Activated-Rechargeable/dp/B0862BBL8V, Retrieved [online] Oct. 24, 2022,pp. 1-10.

Cheerble, "Wicked Ball",https://www.cheerble.com/products/wickedball?variant=31808965476470, Retrieved [online] Oct. 24, 2022.pp. 1-2.

Copol,"Cat Toy, Interactive Cat Toys for Indoor Cats, Automatic Cat Toy with Replace Feather/LED Light/ Bird Chirping, Electric USB Charging 360°Self Rotating Ball, Kitten Feather Toys(Pink)",https://www.amazon.com/Interactive-Automatic-Chirping%EF%BC%8CElectric-Charging-360%C2%B0Self/dp/B09BFDSXD3, Retrieved [online] Oct. 24, 2022,pp. 1-7.

Coy et al., "Why Can't I Resist Those "Puppy Dog" (or "Kitty Cat") Eyes? A Study of Owner Attachment and Factors Associated with Pet Obesity", https://www.mdpi.com/2076-2615/11/2/539, Feb. 19, 2021, pp. 1-12.

Den Uijl, Ingrid, et al. "External validation of a collar-mounted triaxial accelerometer for second-by-second monitoring of eight

(56) References Cited

OTHER PUBLICATIONS behavioural states in dogs." PloS one 12.11 (Nov. 29, 2017): e0188481. https://journals.plos.org/plosone/article?id=10.1371/journal.pone.0188481, retrieved Sep. 23, 2020, pp. 1-9.

Dicola, T., Cat Purr Detection FFT: Fun with Fourier Transforms, https://learn.adafruit.com/fft-fun-with-fourier-transforms/cat-purr-detection, Retrieved [online] Oct. 24, 2022, pp. 1-3.

Dogcarehq,"Best Interactive Dog Toys: Entertainment and Development", Smart Dog Stuff, https://dogcarehq.com/bes-interactive-dog-toys/ retrieved [online] Oct. 24, 2022, pp. 1-33.

FABLE,"The Game—Best Dog Enrichment Toy & Feeder in One", https://fablepets.com/products/the-game, Retrieved [online] Oct. 24, 2022,pp. 1-11.

Griffies, et al., "Wearable sensor shown to specifically quantify pruritic behaviors in dogs",BMC Veterinary Research, Apr. 3, 2018, pp. 1-10.

Hielm-Bjorkman, et al., "Psychometric testing of the Helsinki chronic pain index by completion of a questionnaire in Finnish by owners of dogs with chronic signs of pain caused by osteoarthritis", American Journal of Veterinary Research vol. 70 No. 6, Jun. 2009, pp. 727-734 (8 pages).

International Search Report and the Written Opinion of the International Searching Authority issued in International Application PCT/US2021/043833 dated Oct. 28, 2021.

International Search Report and the Written Opinion of the International Searching Authority issued in International Application PCT/US2022/049209 dated May 15, 2023.

Ladha C., et al., Gaitkeeper: A System For Measuring Canine Gait, Sensors (Basel, Switzerland) provided by Multidisciplinary Digital Publishing Institute (MDPI), Feb. 8, 2017, 17(2):309, pp. 1-23.

Ladha, C., et al. "A step in the right direction: an open-design pedometer algorithm for dogs." BMC veterinary research 14.1 (Mar. 20, 2018): 107. https://bmcvetres.biomedcentral.com/articles/10.1186/s12917-018-1422-3, retrieved Sep. 20, 2020, pp. 1-17.

Partial international search report in PCT/US2022/049209 dated Mar. 14, 2023.

Petgeek, "Interactive Dog Toys, Durable Motion Activated Automatic Dog Bone for Medium & Large Dogs Boredom, Electronic Dog Enrichment Toys to Chase, USB Rechargeable", https://www.amazon.com/PETGEEK-Electronic-Interactive-Automatic-Material/dp/B08B5SP3GP, Retrieved [online] Oct. 24, 2022,pp. 1-11.

Sefon,"Robotic Cat Toys Interactive, 1000 mAh Large Capacity Battery Operated with USB Charging, Auto/RC 3 Mode Timed with 4 Feathers/Birds/Mouse Toys for Indoor Cats, All Floors Carpet Available",https://www.amazon.com/YicoGomo-Smart-Interactive-Toys-Entertainment/dp/B089YT6KG9/ref=cm_cr_arp_d_product_top?ie=UTF8,Retrieved [online] Oct. 24, 2022,pp. 1-7.

Singleton, S., CONTROL4—Home Automation Blog, "How to choose the right home security system",https://www.control4.com/blog/399/how-to-choose-the-right-home-security-system/, Mar. 17, 2017,pp. 1-7.

Skymee, "Owl Robot: Movable Full HD Pet Camera with Treat Dispenser, Interactive Toy for Dogs and Cats, Mobile Control via App", https://www.amazon.com/SKYMEE-Owl-Robot-Dispenser-Interactive/dp/B07YCCYMH4, Retrieved [online] Oct. 24, 2022, pp. 1-11.

Trixie,"Activity Flip Board Activity Strategy Game Dog Toy",https://www.chewy.com/trixie-activity-flip-board-activity/dp/134668,Retrieved [online] Oct. 24, 2022, pp. 1-7.

Tsai, et al., "Generating consumer terminology to describe emotions in pet owners and their pets", Center for Sensory Analysis and Consumer Behavior, Jun. 21, 2020, pp. 1-13.

Vaataja, et al., "Happy Dogs and Happy Owners Using Dog Activity Monitoring Technology in Everyday Life", University of Tampere, Dec. 4, 2018, pp. 1-12.

Vetsens—Activityscope: https://vetsens.co.uk/products/activityscope/, retrieved Sep. 23, 2020, pp. 1-4.

Webb, et al., "What is animal happiness?",New York Academy of Sciences, 2019, pp. 62-76 (15 pages).

Wernimont, et al., "Use of Accelerometer Activity Monitors to Detect Changes in Pruritic Behaviors: Interim Clinical Data on 6 Dogs", www.mdpi.com/journal/sensors, Jan. 16, 2018, pp. 1-12.

White G.A et al., ""Who's been a good dog?"—Owner perceptions and motivations for treat giving", ScienceDirect, Sep. 15, 2016, p. 14-19.

Wickedbone, "Smart Bone, Automatic & Interactive Toy for Dog, Puppy and Cat, App Control, Safe & Durable, Keep Your Pets Entertained All Day", Amazon, (Oct. 7, 2018), Retrieved Oct. 24, 2022, pp. 1-11.

Wiseman-Orr, et al., "Development of a questionnaire to measure the effects of chronic pain on health-related quality of life in dogs", American Journal of Veterinary Research vol. 65 No. 8, Aug. 2004, pp. 1077-1084 (8 pages).

Wiseman-Orr, et al., "Validation of a structured questionnaire as an instrument to measure chronic pain in dogs on the basis of effects on health-related quality of life", American Journal of Veterinary Research vol. 67 No. 11, Oct. 16, 2006, pp. 1826-1836 (11 pages).

Wrigglesworth, David J., et al. "Accuracy of the use of triaxial accelerometry for measuring daily activity as a predictor of daily maintenance energy requirement in healthy adult Labrador Retrievers" Abstract, https://avmajournals.avma.org/doi/abs/10.2460/ajvr.72.9.1151, Sep. 2011, vol. 72, No. 9,retrived Sep. 23, 2020, pp. 1-2.

WWVVPET,"Interactive Cat Toys Ball with LED Light & Catnip, Upgraded Ring Bell Feather Pet Toy, Auto Spinning Smart Cat Ball Toy, USB Rechargeable Stimulate Hunting Instinct Kitty Funny Chaser Roller", https://www.amazon.com/Interactive-Spinning-Rotating-Intelligent-Rechargeable/dp/B08B16V3FN, (Jan. 5, 2021), Retrieved Oct. 24, 2022, pp. 1-9.

Zamkah, et al., "Identification of Suitable Biomarkers for Stress and Emotion Detection for Future Personal Affective Wearable Sensors", https://www.mdpi.com/2079-6374/10/4/40, Apr. 16, 2020, pp. 1-15.

International Search Report and the Written Opinion of the International Searching Authority issued in International Application PCT/US2023/028570 dated Nov. 10, 2023.

\* cited by examiner

SYSTEM AND METHOD FOR ASSOCIATING A SIGNATURE OF AN ANIMAL MOVEMENT AND AN ANIMAL ACTIVITY

BACKGROUND

An animal, such as a pet, is typically unable to communicate to a pet owner or veterinarian the activities performed by the animal. Such activities may include the movements of the animal, the feedings of the animal, the play of the animal, and the waste activities of the animal. Movements of the animal, feedings of the animal, and waste activities of the animal can be manually observed via a pet owner or veterinarian. Such manual observation of the animal can be useful in determining if the animal is eating the desired amount of calories and/or urinating/defecating a desired amount of times, for example. Manual approaches, however, are often cumbersome and do not provide timely diagnosis of the animal's caloric intake and expenditures. Further, manual observation of animals is prone to inaccuracies, incompleteness, and forgetfulness. Thus, what is desired is a method and/or system for automatically determining the eating, drinking, playing, urinating, and defecating behavior of the animal, for example, during a predetermined time period. Such determinations may be used to easily and accurately determine the health (such as gastro-intestinal health) of the animal.

BRIEF SUMMARY

A system, apparatus, and/or method of identifying an activity of an animal. The activity may include the animal drinking, eating, urination, or defecating. Motion data of a first animal may be received, for example, via a sensor. Predetermined signatures of one or more second animals may be received. The predetermined signatures of the one or more second animals may be associated with one or more activities of the one or more second animals. A signature of an activity of the first animal may be determined based on the motion data of the first animal. Based on the signature of the activity of the first animal and the predetermined signatures of the second animal, the activity of the first animal may be identified. The identified activity of the first animal may be displayed via a display device.

BRIEF DESCRIPTION OF THE DRAWINGS

The present invention will become more fully understood from the detailed description and the accompanying drawings, wherein.

DETAILED DESCRIPTION

Figure 1:
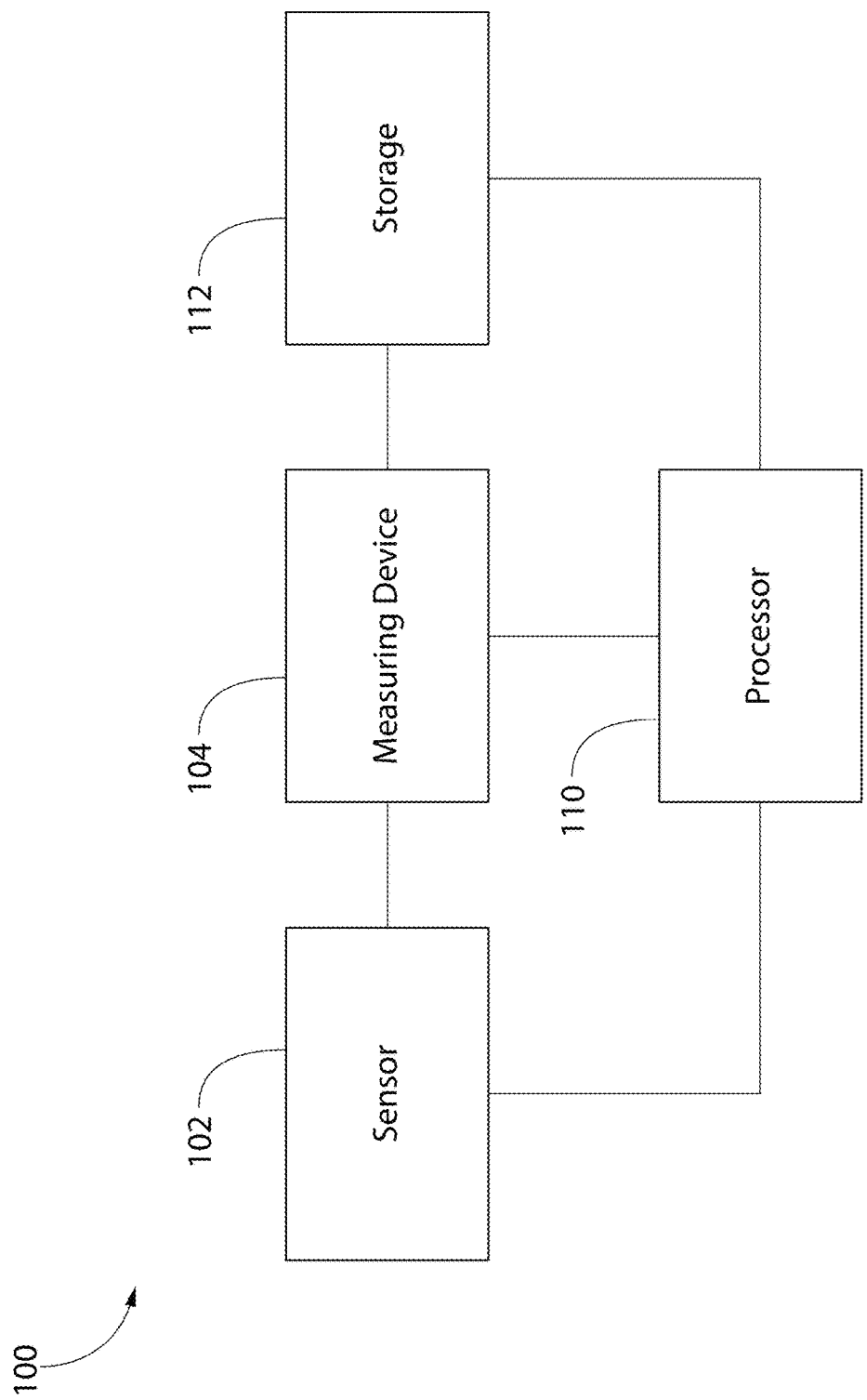
FIG. 1 is a block diagram of a system having a plurality of modules configured to collect and analyze the behavior of an animal.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The system, method, and apparatus seek to provide movement, location, and/or behavior monitoring of an animal, for example, to determine activities of the animal. Activities of the animal may include, for example, the animal drinking, eating, urinating, defecating, vomiting, expelling hairballs, running, walking, jumping, resting, and the like. In examples, other activities of the animal may include the animal playing and/or interacting with other animals or persons. Still other activities may include emotions being exhibited by the animal, such as the animal experiencing fear, anxiety, happiness, aggression, and the like. The system, method, and apparatus seek to automatically determine the activities of the animal to allow real-time assessment and/or continuous observation of response to nutrition therapy provided to the animal, determination (e.g., estimation) of energy intake of the animal, determination (e.g., assessment) of gastrointestinal (GI) health and disease of the animal, determination (e.g., assessment) of stress of the animal, identification of illness and/or aging of the animal, and/or determination urination and/or defecation issues exhibited by the animal.

Example animals may be a pet (e.g., cat, dog, bunny, guinea pig, bird), a farm animal (e.g., a horse, cow, chicken), a zoo animal (e.g., a lion, bear), an animal in the wild, and the like. The activity monitoring of the animal may provide (e.g., automatically provide) an early detection of an abnormality exhibited by the animal. The abnormality may be a caloric abnormality (such as the animal not consuming a sufficient amount of calories to replace calories expended via activity), a health abnormality (such as a sickness, disease, injury, etc.), an activity abnormality (such as the animal is not exercising a predetermined amount), and the like.

Early detection of an animal's abnormality may result in many benefits to the animal, especially if the animal's caretaker or an animal doctor takes corrective action as result of the detected abnormality. The system may be designed for use at the home of the animal and may lead to vital information being provided to the animal's care taker and/or animal doctors. The system may include a device placed on, within, or upon the animal.

Although the disclosure may describe the device being placed on or upon an activity collar of the animal, it should be understood that such example is for illustration purposes only. The device may be worn on one or more of the head of the animal, the ears of the animal, the neck of the animal, the torso of the animal, limbs (e.g., arms, legs) of the animal, the tail of the animal, the mouth (e.g., tooth, cap over the tooth, replacement tooth), the eye (e.g., contact lenses), and the like. The device may be placed in one or implants within the animal, such as implants within the belly and/or base of the tail of the animal, a neuticle of the animal, etc. The system may include one more devices coupled to a collar, harness, bracelet, anklet, belt, earring, headband, and the like. In other examples the system may include one or more devices attached to one or more attachment mechanisms, such as a coat, boot, decorative clothing (e.g., ribbon), sweater, hat, etc. In other examples one or more of the devices and/or mechanisms may be implanted within the animal. For example, one or more of the devices may be a subdermal implant that may be placed underneath the skin of the animal.

The device may be contained within on or more objects, such as one or more objects with which the animal interacts. For example, the device may be contained about a toy of the animal. The device contained about the toy may enable the conditions or behaviors of the animal to be determined. As an example, exploration or play behavior of the animal with the toy may be determined. The device contained about the toy may include one or more devices described herein, such as an accelerometer, Bluetooth, and/or RFID. The device may interact with one or more devices (e.g., sensors), similar to a proximity beacon. Upon determining that the animal is or was performing a behavior (such as chewing or licking) and that the animal is or was proximate the toy when performing the behavior, it may be determined that the animal is or was engaging in play.

A recognition device (e.g., on the device worn by the animal) may identify the animal within the system. The animal may be linked to an animal profile. The animal's movements (e.g., accelerations, velocities, and the like), locations, and/or behaviors may be monitored, tracked, and/or electronically recorded (e.g., automatically monitored, tracked, and/or electronically recorded) on a predefined basis (e.g., on a daily, weekly, monthly, yearly basis). The animal's movements, locations, and/or behaviors may be used to determine activities of the animal, such as drinking events, feeding events, chewing events, licking events, barking and/or growing events, urination events, defecation events, running events, body wiggling events, tail wagging events, jumping events, resting events, etc. The activity level, caloric condition (e.g., whether the animal is consuming enough calories to replace calories lost via activity and/or whether nutritional therapy provided to the animal is providing desired remedial effects), and/or health condition (such as whether the animal is experiencing unhealthy symptoms, such as abnormal GI symptoms) may be determined based on the animal's movements and/or locations. The animal's movements, locations, and/or behaviors may be monitored, tracked, and/or recorded without disturbing the animal or disrupting its natural behavior. For example, as animals may travel to their feeding area or waste area on their own terms, and on their own schedule, the movements and/or locations of the animal at the feeding area and/or waste area may be used to determine the animal's condition without detection by the animal.

In an example, the monitoring of the animal's movements, location, behaviors, and/or condition may be performed via collection of one or more types of data. The data may include motion data, location data, orientation data, spatial data, weight data, and the like. The data may be collected and/or monitored during one or more pet activities, such as eating, drinking, resting, running, urinating, and/or defecating. The data (e.g., acceleration data, velocity data, location data, etc.) may represent movements of the animal in one or more directions, such as in the X, Y, and/or Z direction. The data may represent a signature of an animal's activity. For example, tri-axial acceleration data of an animal in the X, Y, and/or Z direction may represent a signature of an animal's activity. Each activity of the animal may have signatures that differ from one or more other activities. For example, an animal drinking may have a signature (e.g., a unique signature), an animal eating may have a signature (e.g., a unique signature), an animal urinating may have a signature (e.g., a unique signature), an animal defecating may have a signature (e.g., a unique signature), an animal resting may have a signature (e.g., a unique signature), an animal walking may have a signature (e.g., a unique signature), an animal running may have a signature (e.g., a unique signature), an animal jumping may have a signature (e.g., a unique signature), an animal communicating (e.g., barking) may have a signature (e.g., a unique signature), an animal scratching and/or digging may have a signature (e.g., a unique signature), etc. One or more (e.g., each) signature may be different than, or the same as, one or more signatures.

Data (such as the collected/monitored data and/or signature data related to the collected/monitored data) may be stored in a repository that may be accessible to animal caregivers, veterinarians, and the like. The data may be accessible via a portable electronic device (e.g., an application of a portable electronic device) and/or a server. A portable electronic device may be one or more of a number of devices, including without limitation, a smart phone, a cell phone, a tablet computer, a personal digital assistant ("PDA"), a laptop computer, etc. As described herein, the data may be analyzed to identity behavior and/or habits of the animal, and to provide the data and/or advice to owners based on the data. The behavior and/or habits of the animal may be identified via a signature representing an activity of the animal.

The data may be monitored, collected, and/or generated over time, for example, for statistical processing of the animal's behaviors and/or habits. The data collected and/or generated over time may be used to generate signatures of the animal over time. The data may be compared with previously collected and/or stored data for purposes of understanding the animal's activity, consumption, evacuation, and/or health trends. Signatures (e.g., signatures of animal behavior) may be compared with previously monitored, collected, and/or generated signatures. The data (such as the collected data and generated signatures) may be compared with previously collected, generated, and/or stored data for determining variations in an animal's state of health, for determining whether a health abnormality exists for the animal, for determining whether an action (e.g., a nutrition remediation, nutrition therapy, nutrition intervention, nutritional support, etc.) is correcting the animal's condition, etc. The previously collected and/or stored data may relate to the animal that is being monitored and/or the previously collected and/or stored data may relate to an animal other than the animal being monitored (e.g., for comparison purposes).

As described herein, an animal's actions with respect to eating, drinking, urinating, defecating, and/or resting may be monitored for determining the caloric requirements and/or expenditures of the animal, to determine if therapy (such as nutritional therapy) is desired or is providing remedial effects on the animal, to determine if the animal has a health abnormality, etc. For example, an animal being managed (e.g., by the caregiver or an animal doctor) via medicinal and/or food products for a health abnormality may be observed and/or monitored to determine if the management is improving the animal's condition.

The movements of the animal may be identified to determine the activity level of the animal. The activity level may determine whether the animal is receiving exercise above (or below) a predetermined recommended level, can determine the amount of calories exerted by the animal, etc. Such movements of the animal may include the forward/rearward motion of the animal, climbing of the animal, jumping of the animal, etc. As another example, an animal that is identified to be jumping may be determined to be a healthy animal, while an animal that is identified to not jump may be determined to be an unhealthy animal, such as an animal that has an injured appendage or other body part. The parameters monitored and stored over time (e.g., as historical data) may be used by an animal doctor and/or the caretaker to assess trends and changes in the animal's state of activity, caloric consumption and exertion, and/or health over time.

An animal's condition, such as the animal's state of activity, caloric consumption and exertion, and/or health over time may be determined and/or recorded. Whether the animal is determined to be suffering from an injury, an illness, a disease, etc., may be recorded. Parameters relating to the animal's activity level, caloric consumption and exertion, and/or health may include the amount of times the animal runs, walks, jumps, eats, drinks, sleeps, urinates, and/or defecates in a time period. The duration of the running, walking, jumping, eating, sleeping, urination, defecation, etc. of the animal during a time period may be used to determine the animal's state of activity, caloric consumption and exertion, and/or health over the time period. As an example, the time period may be an hour, a day, a week, a month, or the like.

Application of statistical methods may be used to derive information about the animal's condition. For example, an animal (e.g., a healthy animal, such as an animal not suffering from illness, disease, stress, etc.) may be expected to run, jump, drink, eat, sleep, urinate, and/or defecate a minimum and/or maximum amount of times during a time period. Heath conditions of an animal may include, but not be limited to, weight (e.g., controlling obesity) control, allergies, kidney diseases, orthopedic conditions, endocrine diseases (such as diabetes), skin and coat health, gastrointestinal (GI) issues, cystitis/urinary tract diseases, liver diseases, dental issues, vomiting, hairballs, itching, shaking, and the like. A condition of the animal may include the animal performing an action, such as caring for itself (via self-grooming (e.g., licking) itself). Nutritional therapy may be used to remedy one or more health conditions of an animal. An animal receiving nutrition therapy and/or nutrition support (e.g., to assist in the management of a medical condition, weight management, or a life-stage related issue) may be expected to run, jump, drink, eat, sleep, urinate, and/or defecate a minimum and/or maximum amount of times during a time period. Nutrition therapy may be used to manage signs of one or more conditions of an animal, such as a weight-related issue (e.g., managing overweight or obesity), food or environmental allergy, kidney or bladder disease, orthopedic condition, endocrine disease (such as diabetes, hypo- or hyperthyroidism), skin and coat conditions, gastrointestinal (GI) conditions, cystitis/urinary tract disease, liver disease, dental issues, behavioral issues or life stage-related issues (growth and/or development, pregnancy and/or lactation, aging and/or dementia, etc.) and the like, of an animal.

A mean, median, range, and/or variability (e.g., standard deviation, variance, z-scores, etc.) of the above parameters may be defined for a healthy animal and/or for an unhealthy animal. If the animal performs a defined health parameter less than or more than an amount defined for a healthy animal, the animal may be identified as being unhealthy (e.g., a sick, injured, diseased, etc.). Subsets of characteristics of the animal may be used to determine whether an animal's behaviors and/or habits are indicative of a healthy animal or an unhealthy animal. Such characteristics may include the species, body type (e.g., long, short, thin, stocky), breed, age, sex, geographic location, size/weight, of the animal.

Parameters determined, identified, received, and/or transmitted may be recorded. The parameters may be recorded continuously, for example, from the moment of system activation throughout animal's life. In other examples, the parameters may be recorded for a predefined time period (e.g., for a day, a week, a month, etc.), on a predefined frequency (e.g., every weekday), etc.

FIG. 1 shows an example system for monitoring an animal's movement, location, behavior, health, habits, and/or other characteristics. Although FIG. 1 shows system 100 including a sensor 102, a measuring device 104, and/or a storage device 112, it should be understood that this if for illustration purposes only and system 100 may include fewer, the same, or more devices than shown on FIG. 1.

Sensor 102 may be configured to detect the motion (or stillness) of an animal, to detect an activity level of the animal, to detect an orientation of the animal, to detect a location of the animal, etc. Sensor 102 may be one or more of a variety of form factors, including, but not limited to, an accelerometer, a gyroscope, a magnetometer, force transducers, displacement transducers, pressure transducers, force sensors, displacement sensors, pressure sensors, load cells, photographic cameras, video cameras, camcorders, and a combination thereof. In examples, sensor 102 may include one or more of thermometers, electrocardiography (ECG), photo plethysmography (PPG) devices, microphones, respiratory inductive plethysmography (RIP) devices, optoelectronic plethysmography (OEP) devices, or transthoracic impedance devices. For example, caloric expenditure may be assessed by heat produced, by cardiac/respiratory output, distance traveled, and/or step metrics.

ECG and PPG may provide pulse/heart rate detection. Microphones, RIP, OEP and impedance may provide a breathing rate.

In addition, or alternatively, sensor 102 may be one or more of optical sensors, optical reflecting sensors, LED/photodiode pair optical sensors, LED/phototransistor pair optical sensors, laser diode/photodiode pair optical sensors, laser diode/phototransistor pair optical sensors, optocouplers, optical fiber coupled optical sensors, magnetic sensors, weight sensors, force sensors, displacement sensors, pressure sensors, various proximity sensors, such as inductive proximity sensors, magnetic proximity sensors, capacitive proximity sensors, and/or a combination thereof. Sensor 102 may include communication circuitry, such as Bluetooth (e.g., classic Bluetooth and/or Low Energy Bluetooth), RFID, Wi-Fi, and other wireless technologies. Sensor 102 may communicate with one or more devices, for example, sensor 102 may communicate with a server.

Measuring device 104 may be configured to measure a characteristic related to the animal. Measuring device 104 may be implemented in one or more of a variety of form factors, including, but not limited to, weighing scales, weight transducers, force transducers, displacement transducers, pressure transducers, weight sensors, force sensors, displacement sensors, pressure sensors, real time clocks, timers, counters, and/or a combination thereof. Measuring device 104 may include communication circuitry, such as Bluetooth, RFID, Wi-Fi, Medical Implant Communication System (MICS) (e.g., a hybrid of the technologies, such as MICS/Bluetooth), and other wireless technologies. Measuring device 104 may communicate with one or more devices, for example, measuring device 104 may communicate with a server.

Storage device 112 may be configured to store data provided to and/or from system 100. The data may include motion data and/or location data provided by the sensor 102, for example. Example storage devices 112 may be memory devices, data storage devices, and a combination thereof, such as memory chips, semiconductor memories, Integrated Circuits (IC's), non-volatile memories or storage device such as flash memories, Read Only Memories (ROM's), Erasable Read Only Memories (EROM's), Electrically Erasable Read Only Memories (EEROM's), Erasable Programmable Read Only Memories (EPROM's), Electrically Erasable Programmable Read Only Memories (EEPROM's), an Electrically Erasable Programmable Read Only Memory (EEPRO), volatile memories such as Random Access Memories (RAM's), Static Random Access Memories (SRAM's), Dynamic Random Access Memories (DRAM's), Single Data Rate memories (SDR's), Dual Data Rata memories (DDR's), Quad Data Rate memories (QDR's), microprocessor registers, microcontroller registers, CPU registers, controller registers, magnetic storage devices such as magnetic disks, magnetic hard disks, magnetic tapes, optical memory devices such as optical disks, compact disks (CD's), Digital Versatile Disks (DVD's), Blu-ray Disks, Magneto Optical Disks (MO Disks) and/or a combination thereof. In one embodiment, the storage device comprises a semiconductor RAM IC for an intermediate recording of the behavior, health, and/or characteristics of the animal, and then transfer of the data to a flash memory IC for non-volatile recording. Storage 112 may be an external memory device, such as a USB flash memory, an external hard drive, etc.

System 100 may include a processor 110 configured to calculate and/or process data provided to system 100, for example. Example processors may be electronic circuits, systems, modules, subsystems, sub modules, devices and combinations thereof, such as Central Processing Units (CPU's), microprocessors, microcontrollers, processing units, control units, tangible media for recording and/or a combination thereof. Storage device 112 may be configured to store derived data from the processor 110. Processor 110 may include communication circuitry, such as Bluetooth, RFID, Wi-Fi, Medical Implant Communication System (MICS) (e.g., a hybrid of the technologies, such as MICS/Bluetooth), cellular based location systems, and other wireless technologies. Processor 110 may communicate with one or more devices, for example, processor 110 may communicate with a server.

In an example, sensor 102, measuring device 104, and/or storage 112 may be assembled in a number of configurations, including in a stand-alone apparatus. In another example, sensor 102, storage 112, and processor 110 may be assembled in a stand-alone apparatus. In other examples, the processor 110 and/or storage 112 may be configured as remote devices, such as remote servers (e.g., cloud storage devices). Although FIG. 1 shows a connection between processor 110 and each of sensor 102, measuring device 104, and storage 112, examples should not be so limited. In examples one or more of the devices may communicate with one or more (including any, or none) of the other devices. For example, sensor 102 may communicate with processor 110 and storage 112, sensor 102 may not communicate with measuring device 104, etc. One or more devices may be added and/or removed from system 100. For example, additional sensors 102 may be added to system 100 and/or measuring device 104 may be removed from system 100.

Data relating to the animal may be processed and/or recorded for a determination of the animal's movement, location, activity level, caloric expenditures and/or consumption, and/or health condition. For example, the amount of times, durations, etc., that an animal runs, eats, drinks, urinates, defecates, and/or rests may be used to determine if the animal is running at a predetermined level desired for a healthy animal, if the animal is eating more than a predetermined amount of times desired for a healthy animal, if the animal is defecating above or below a predetermined amount of times, and/or if the animal is eating or defecating for a longer or shorter duration per instance (e.g., as straining to defecate may take a longer time than a normal bowel movement) desired for a healthy animal. A weight of an animal, a weight of a waste deposited by an animal (e.g., in a waste area), a body temperature of an animal, a weight of the food and/or liquid consumed by the animal, the date of an event (e.g., an eating, drinking, defecating, urinating), the time of an event (e.g., an eating, drinking, defecating, urinating), and/or the time of a movement of the animal may be used to determine a health condition of an animal. The animal's use of a clothing, apparatus, etc., may be used to determine the activity level, caloric expenditures and/or consumption, and/or health condition of an animal. For example, the animal's wearing of a bootie, use of an enclosure (e.g., joint enclosure, such as a knee/elbow enclosure), a harness, etc. may be used to determine the activity level, caloric expenditures and/or consumption, and/or health condition of the animal. One or more activities of the animal may be recorded via a video recording, picture, and/or audio recording and/or may be processed.

Figure 2:
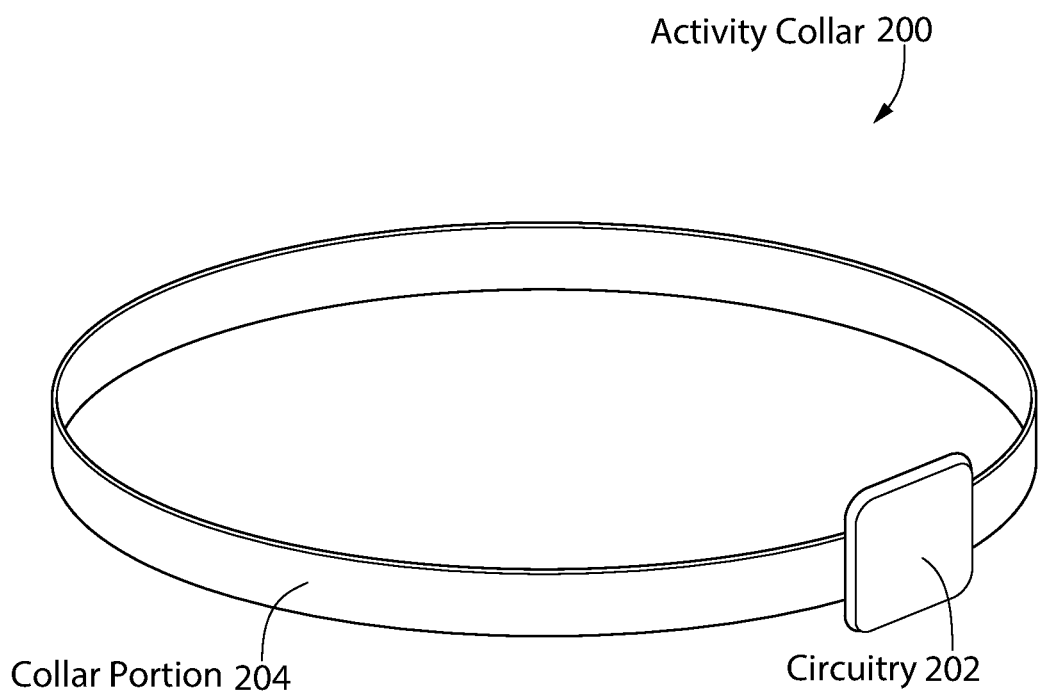
FIG. 2 is a perspective view of an example activity collar.

FIG. 2 is a perspective view of an example activity collar 200. Activity collar 200 may be linked to a particular animal (e.g., may be linked to a profile of a particular animal). Activity collar 200 may include circuitry 202 that is added to a collar portion 204. The circuitry 202 may include a processor, storage, wireless communication hardware, one or more sensors (e.g., accelerometers, gyroscopes, magnetometers, etc.), GPS, temperature sensors, moisture detectors, biometric sensors, etc. The wireless communication hardware may include a transmitter and a receiver. For example, the wireless communication hardware of the activity collar 200 may include a low energy communication device, such as Bluetooth Low Energy or RFID. The activity collar 200 may include a memory for storing data.

An accelerometer located on the activity collar 200 may be configured to measure motion(s) of the animal, such as tri-axial accelerations of the animal in the XYZ coordinate space. Accelerations of the animal, changes in velocity of the animal, and/or changes in position of the animal may be measured and/or determined. A gyroscope may be configured to measure changes in orientation of the animal and/or changes in rotational velocity of the animal. A magnetometer may be configured to measure orientation (e.g., absolute orientation) of the animal, for example, in the NESW plane. By determining the accelerations, velocities, changes of position, orientations, etc., of the animal, the movements of the animal (such as the gait of the animal) may be determined.

The activity collar 200 may include a location sensor, as described herein. For example, the activity collar 200 may include a GPS and/or a photo electric sensor that may track a position of the animal. For example, the GPS and/or photo electric sensor may indicate that the animal is within the waste area. When the animal enters the waste area, for example, automated alerts may be sent to the system to perform monitoring (e.g., monitoring of motion, orientation, and the like) of the animal via one or more sensors (e.g., accelerometer, gyroscope, proximity sensor, etc.). To save on battery life of the activity collar, for example, one or more of the devices within the activity collar may activate (e.g., only activate) when the animal crosses the perimeter. One or more sensors within the activity collar may only activate when the animal is within a waste area, about a waste area, and/or within a feeding area.

Activity collar 200 may send data relating to an animal to a server, feeding bowl, water dish, litter box, and/or other location, such as a prohibited area, an area where the animal may exhibit certain behaviors (e.g., anxiety behaviors such as pacing or destructive behaviors such as in front of a door or window), in a preferred location such as a kennel or resting/sleeping area, etc. For example, activity collar 200 may send motion data, orientation data, location data, etc., to a server, feeding bowl, water dish, and/or litter box. The server may perform computations of the data, for example, to determine an animal activity, a motion of the animal, a signature of the animal, and the like. The server may be configured to communicate the data to the user and/or to one or more other parties (e.g., a veterinarian, spouse, etc.). In examples, a portable electronic device may perform computations of the data, for example, to determine an animal activity, a motion of the animal, a signature of the animal, and the like. The portable electronic device may be configured to communicate the data to the user and/or one or more other parties (e.g., a veterinarian, spouse, etc.).

The activity collar may have a biometric monitoring sensor. The biometric monitoring sensor may be configured to determine body measurements and/or calculations of the animal. For example, temperature sensor and/or heart rate sensor may be used to determine the body temperature of the animal and/or the heart rate of the animal. The biometric monitoring sensor may be located on a device (e.g., the activity collar), within the animal (such as implanted within the animal), or on another device position on or about the animal.

Figure 3A:
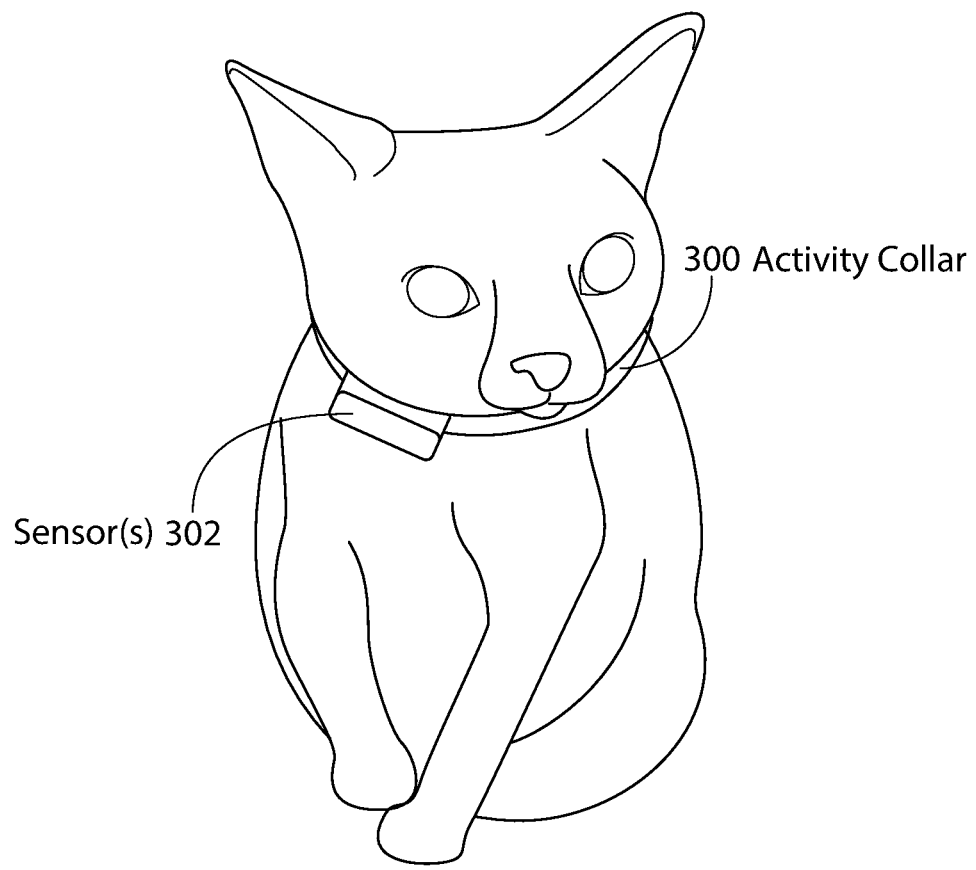
FIG. 3A is a depiction of an animal wearing an example activity collar of FIG. 2.
Figure 3B:
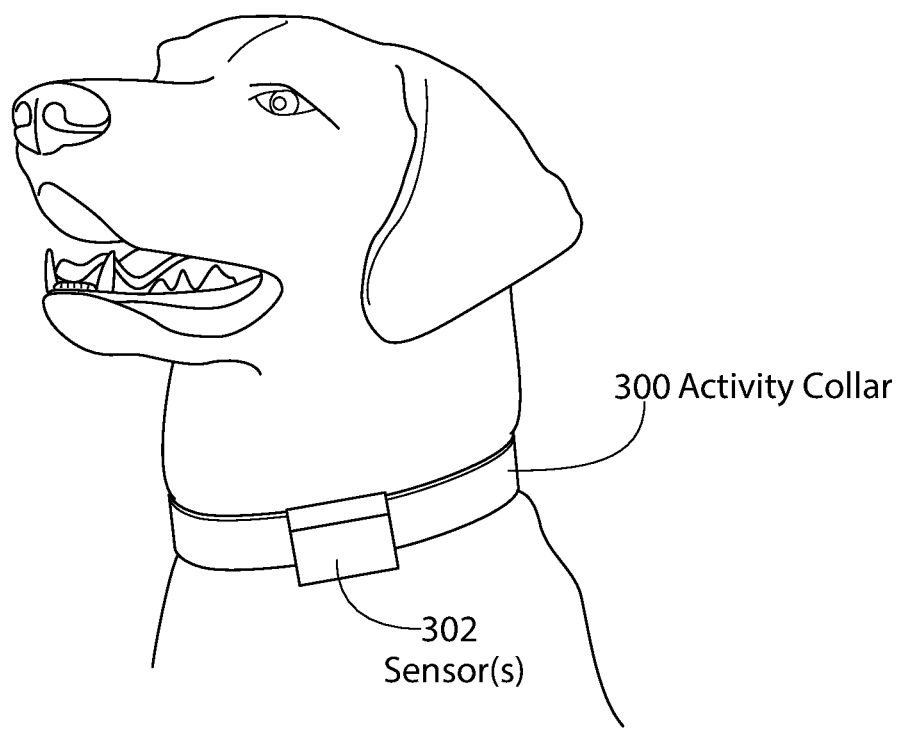
FIG. 3B is a depiction of an animal wearing another example activity collar of FIG. 2.

FIGS. 3A, 3B show example uses of the activity collar 300. As shown on FIG. 3A, a cat may wear the activity collar 300. As shown on FIG. 3B, a dog may wear the activity collar 300. Although the examples shown on FIGS. 3A, 3B is a collar, it should be understood that the activity collar is for illustration purposes only and may be any wearable device that may come in other form factors besides a collar and worn by other animals besides a cat and a dog. For example, activity collar may be a jacket, vest, hat, gloves, contact lenses, rings (e.g., earrings), or any other device (or combinations of devices) that can be worn on the outside (or inside) of an animal.

As described herein, the activity collar 300 may have one or more sensors 302, such as an accelerometer. The sensor 302 may be coupled to the activity collar, for example, on an outside of the activity collar 300. In other examples, the sensor (e.g., accelerometer) may be integrally formed within the activity collar 300. As shown on FIG. 3, a location sensor 310 may be included in the system. The location sensor 310 may be located on the animal (e.g., worn by the animal) or positioned upon a surface that is not the animal. The location sensor 310 may be a proximity sensor. For example, a proximity sensor may be used to determine if the animal is near a predefined area, such as a feeding bowl, water bowl, and/or waste area.

The sensors and other devices may be used to determine whether an animal is performing an animal activity (e.g., running, jogging, jumping, urinating, defecating, drinking, eating, resting, sleeping, etc.). An animal's urination and/or defecation behaviors and/or habits may be determined based on motion data, orientation data, location data, etc., of the animal.

As described herein, the animal's eating, drinking, urination, defecation, and/or rest may be determined based on motion data (e.g., if one or more parts of the animal are moving), orientation data (e.g., if one or more parts of the animal, such as the animal's head, is pointed in a downward direction). The animal's eating, drinking, urination, defecation, and/or rest may be determined based on location data (e.g., if the animal is near the waste area, the eating area, the drinking area, the resting area (e.g., a bed), etc. The animal's eating, drinking, urination, defecation, and/or rest may be determined based on a combination of location data and motion data (e.g., if the animal is near the food dish and the head is pointed towards a food dish).

Based on one or more of the animal's motion, location, orientation, etc., a signature of an activity of the animal may be determined. An animal activity (e.g., whether an animal is urinating, defecating, eating, drinking, and/or resting) may be determined based on one or more signatures of the animal. The signatures of the animals may be a scratching, turning (e.g., in circles), a crouching, a sniffing, a defection posture, a urination posture, a peristaltic movement, and the like. Unsuccessful urinations and/or successful urinations may be determined via a signature. Unsuccessful defecations and/or successful defecations may be determined via a signature. Signatures may be used to determine a non-event, such as an event proximate to the feeding, drinking, waste, and/or rest area that are not related to eating, drinking, urinating, defecating, and/or resting, respectively. One or more activity levels, caloric expenditures and/or consumptions, and/or health conditions (e.g., diseases, illness, injuries, etc.) of the animal may be detected based on a signature of the animal.

As described herein, a signature of the animal's activity may be determined using monitored, collected, and/or generated data (such as monitored, collected, and/or generated tri-axial acceleration data). For example, motion data of the animal may be collected from a sensor, such as an accelerometer. The motion data may include acceleration data (e.g., tri-axial accelerometer behavior data), velocity data, location data, and the like, of the animal. The motion data (such as the accelerometer data) may be associated with a signature of an activity. For example, accelerometer data of an animal may be associated with a signature of an animal drinking, eating, urinating, and/or defecating.

Figure 4A:
FIGS. 4A, 4B are example screenshots of a use of the system of FIG. 1.
Figure 4B:
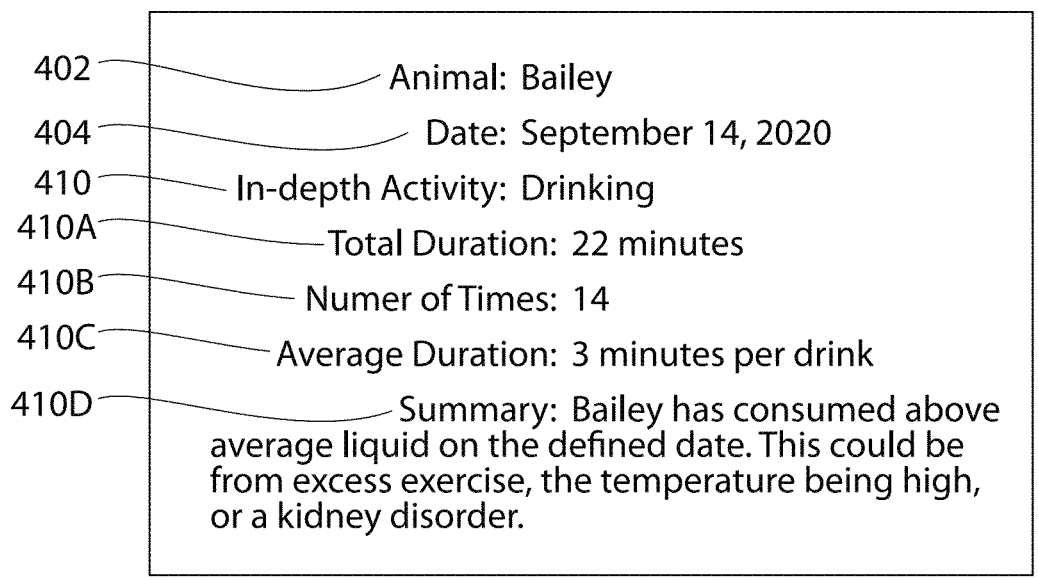

FIGS. 4A, 4B show example screenshots of a use of the animal monitoring system. The screenshots may be provided on a portable electronic device, for example. The screenshots provide notifications to the user of animal activities (e.g., urinating, defecating, eating, drinking, running, trotting, resting, sleeping, vomiting, regurgitating, drooling, snoring, panting) of the animal. The notifications and animal activities shown on the screenshots are for illustration purposes only and are not limiting. In examples, other notifications and/or other animal activities may be provided to the user.

FIG. 4A shows an example screen shot of data collected by an activity collar (such as activity collar 200) worn by an animal. Category 402 shows an identification of the animal. The identification of the animal can be the name of the animal (such as the name Bailey), the body type of the animal, the breed of the animal, a unique code (e.g., number and/or letter of the letter of the animal), etc. Category 404 shows the date, such as the date in which an activity of the animal has been monitored. Although 404 shows a date, in examples category 404 may be a date, a day, a time, a time of year (e.g., summer, winter), a range of dates, a range of days, a range of times, and the like.

Category 406 may provide information relating to the animal, such as the body type of the animal, breed of the animal, the gender of the animal, the age of the animal, disorders and/or conditions relating to the animal, and the like. Category 408 may show the activity of the animal, such as the activity of the animal being monitored during category 404. Category 408 may include the duration(s), time (s), periodic(s) in which the animal has performed the activity. FIG. 4A shows an example in which a golden retriever named Bailey on Sep. 14, 2020 has Eaten 408A for 75 minutes, Drank 408B for 22 minutes, Urinated 408C for 15 minutes, and Defecated 408D for 6 minutes.

FIG. 4B provides additional information relating to an activity provided on FIG. 4A. Categories (such as categories 402 and 404) shown on FIG. 4B may be similar to the categories in FIG. 4A, and thus additional description is unnecessary for these categories. Using the example shown on FIG. 4B, category 410 may relate to an in-depth category of drinking (such as the drinking activity 408B shown on FIG. 4A). Drinking data may be provided for a time period, such as time period 404, although drinking data may be provided for other time periods in examples. FIG. 4B shows the total duration 410A in which Bailey has drank (e.g., 22 minutes) on Sep. 14, 2020. FIG. 4B further shows that Bailey has drank a total of 14 times 410B on Sep. 14, 2020, and the average duration 410C of each of Bailey's drinking activities was 3 minutes.

Based on the monitored activities of the animal, one or more attributes may be determined and/or provided. For example, based on the monitored activities of the animal a health condition of the animal may be determined and/or provided. The monitored activities of the animal may be used for one or more other purposes, such as for training of the animal. As an example, the monitored activities may be used to train an animal not to eat from an unwanted source (e.g., the trash, the table) and/or to refrain from unwanted activities (such as digging in the yard). The monitored activities of the animal may be used to assist in housetraining of the animal, and the like.

FIG. 4B provides an indication of whether the animal's activity indicates a healthy, unhealthy, or underdetermined health condition. For example, as shown on FIG. 4B, summary 410 provides an indication that Bailey has consumed an above average amount of liquid on the provided date. In examples the summary 410 may provide one or more reasons for the animal consuming an amount of liquid. For example, as shown on FIG. 4B, the summary may indicate that the above average amount of liquid consumed by Bailey may be from Bailey exercising excessively, an environmental condition (such as the temperature being high), or a health disorder (such as a kidney disorder). Other data (such as urinating data of the animal) may be used with the drinking data to see if there is an anomaly with the animal's activity, for example, in addition to the urination anomaly. One or more other types of data may be used (e.g., may also be used) to confirm an anomaly in addition to the urination anomaly.

As described herein, data (e.g., motion data, movement data) of the animal may be monitored for determining the activities of the animal. Such activities may include the animal running, defecating, drinking, eating, etc. The movement data of the animal may include acceleration data of the animal, velocity data of the animal, location data of the animal, and the like. In particular, one or more portions (e.g., XYZ components) of data (e.g., acceleration data, gyroscope data, etc.) may form a signature that correlates to an activity of an animal. The one or more portions of acceleration and/or the signature may be monitored for determining the activities of the animal.

Figure 5A:
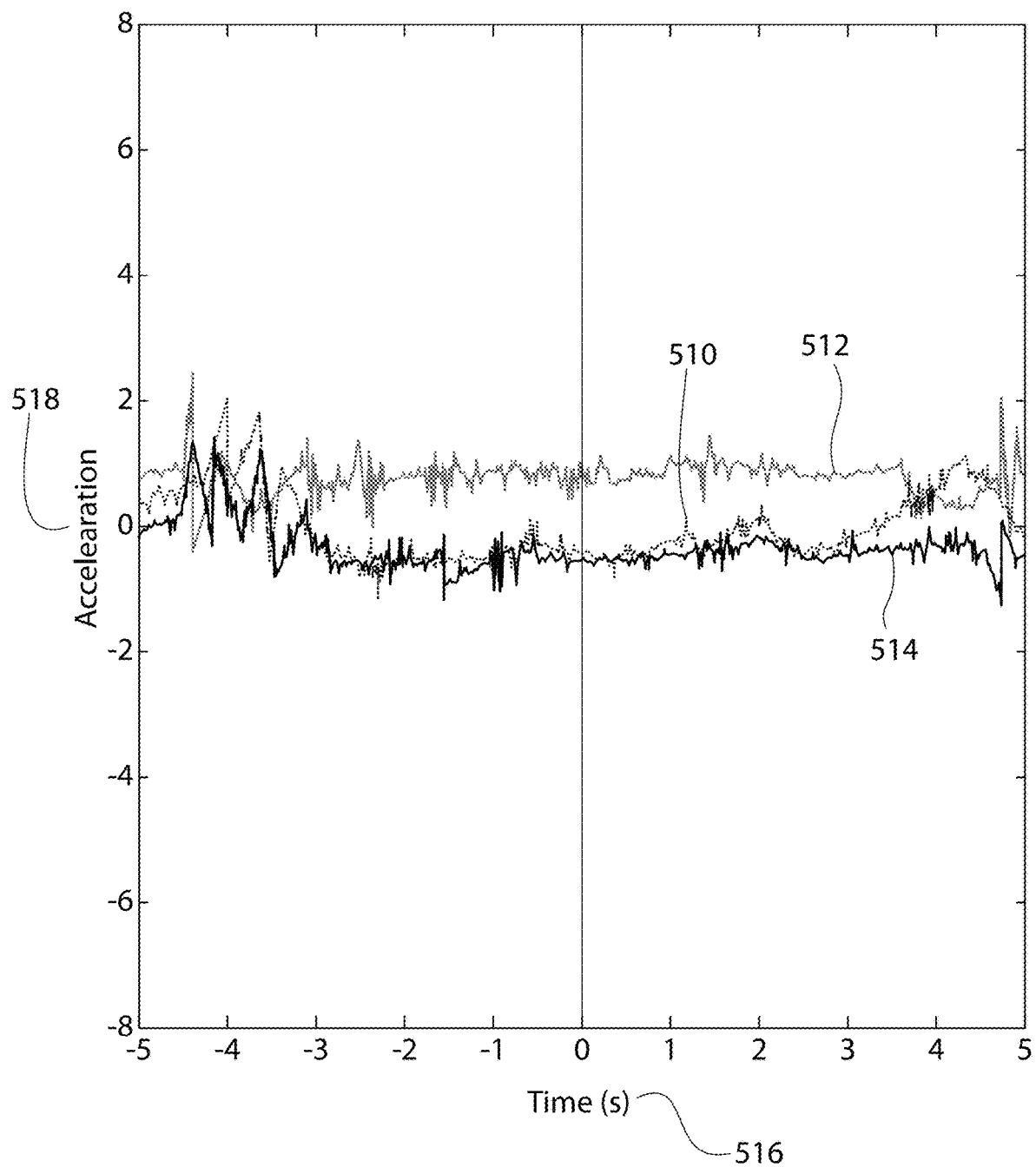
FIGS. 5A, 5B are example signatures of activities of an animal captured by the system of FIG. 1, as described herein.
Figure 5B:
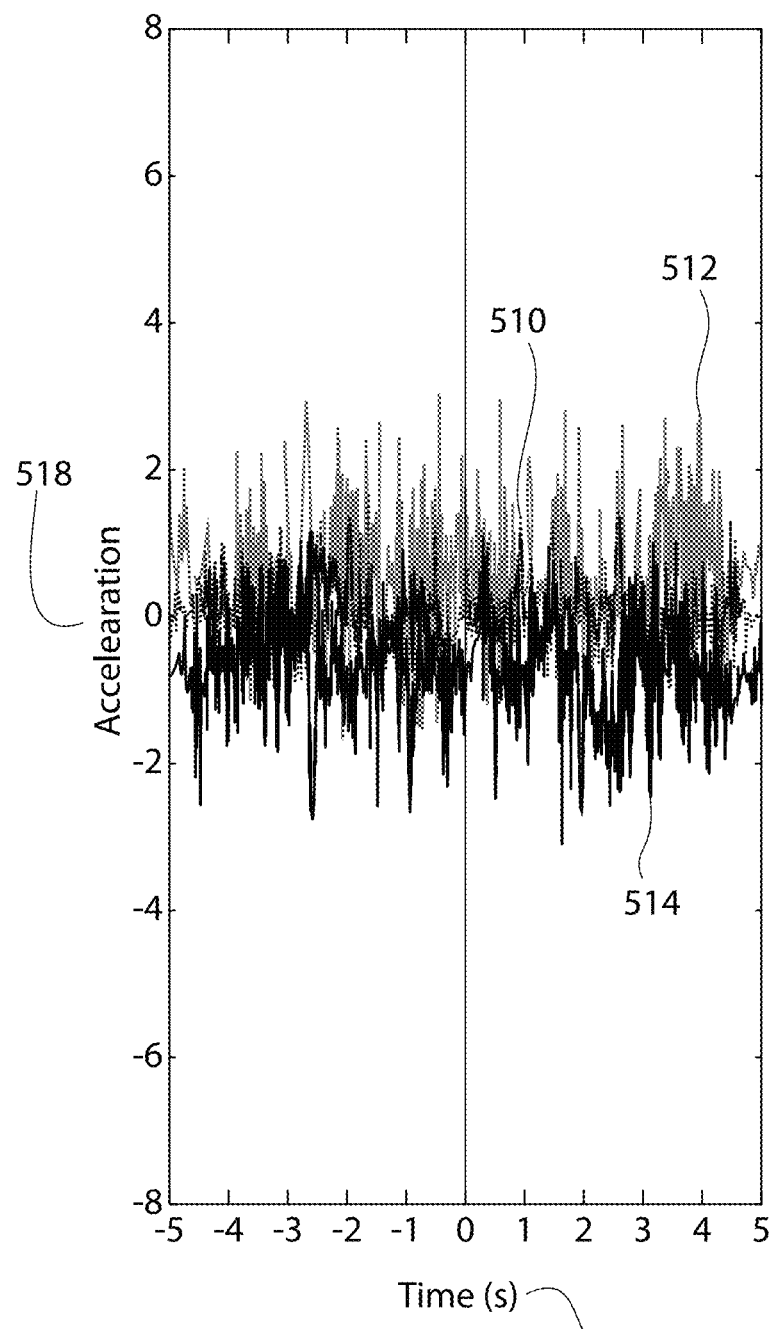

FIGS. 5A and 5B show example motion data (tri-axial acceleration data) relating to signatures of animals. FIG. 5A shows example tri-axial accelerometer data (e.g., signatures) of an animal scratching, and FIG. 5B shows example tri-axial accelerometer data (e.g., signatures) of an animal running. X, Y, and/o Z components of the tri-axial accelerometer data may be associated with a signature and/or may be used to determine an activity of an animal. Although FIGS. 5A, 5B show signatures of an animal scratching and running, it should be understood that this data and/or signatures are for illustration purposes only and other data and/or signatures of animals may be generated and/or identified. For example, generated and/or identified signatures of animals may include an animal drinking, eating, urinating, defecating, walking, trotting, resting, digging, jumping, and the like.

As shown on FIGS. 5A and 5B, motion data may include tri-axial acceleration data in the X 510, Z 512, and Z 514 directions. One or more portions of the motion data may be monitored for a predefined period of time, such as time 516. One or more portions of the motion data (the tri-axial acceleration data) may relate to a signature of an animal, such as a cat, dog, and the like. The motion data and/or signature of the animal may be compared with previous samples of motion data and/or signatures, for example, to determine the activity in which the motion data and/or signature relates. The previous samples of motion data and/or the previous samples of signatures may be associated with an activity of an animal. For example, previous samples of motion data and/or previous samples of signatures may be associated with (e.g., previously associated with) an activity of an animal. Previous samples of motion data and/or previous samples of signatures may be associated with an activity of an animal via manual identification (such as a user manually associating an activity with a signature) and/or via automatic identification (such as a processor associating an activity with a signature). Previous samples of motion data and/or previous samples of signatures may be associated with an activity of an animal via machine learning techniques, such as training a machine learning model.

As described herein, an activity may be associated (e.g., automatically associated) with a signature via machine learning techniques, such as unsupervised or supervised machine learning techniques, deep convolutional neural networks, etc. As an example, a machine learning model may be trained with previously collected motion data (such as motion data having a signature) and identified animal activities. The machine learning model may learn the signatures of the animal activities during this training. Based on learning the signatures of the animal activities, the machine learning model may identify present and/or future motion data and/or signatures of animals as an animal activity.

The machine learning model may take data recorded from one or more sensors, such as one or more accelerometers, gyroscopes, magnetometers, etc., as inputs. The machine learning model may receive labelled behavior data as inputs to determine trends and/or norms of animal activities. The machine learning techniques may be used to determine changes in a health status of an animal, such as a deviation from a pattern derived from the data, while bearing no intuitive association with the health of the animal. The machine learning model may identify deviations from standard forms of a given signature to identify abnormalities in the mode of performance of the behavior, e.g., gait sidedness, elevated intensity of scratching, etc.

The previously collected samples of motion data having a signature may be associated with an animal having similar characteristics of the animal being monitored (e.g., currently being monitored). For example, the previously collected samples of motion data and/or signature may relate to animals being of a similar species, breed, age, sex, and the like, of the animal being monitored (e.g., currently being monitored). In other examples, the previous samples of motion data and/or signatures may include generic information that relates to animals other than the animal being monitored, such as motion data and/or a signature for a generic dog that is used for a collection of dogs. As described herein, the motion data and/or signature may be compared with one or more previously generated signatures to determine the activity of the animal.

Mathematical and/or algorithmic techniques, such as timeseries, bivariate, multivariate and trend analysis, may be used to formulate a trend of the animal activities (e.g., feeding, drinking, urinating, defecating, sleeping). Data collected over time and processed can represent a typical profile of behavior and habits of an animal. The behavior and habits of the animal may be used to determine the animal's health condition. For example, an injured or otherwise ill animal may exhibit different defecating habits than a healthy animal. Trend analysis may be used to determine whether the monitored behavior, habits, etc. of the animal are random, or whether a trend may be developing.

Data may be captured by periodically sampling a sensor or sensors, such as a motion sensor (e.g., an accelerometer, gyroscope, or the like), a proximity sensor (e.g., such as a camera or the like), etc. An array of digital data may be processed, for example, to determine an animal activity (e.g., feeding, urination, defecation, or rest of the animal). The data may be processed via a device on-the-fly (e.g., applying methods as the data samples are encountered by the device and not storing the entire data). Data may be stored by the device (in full length or a portion). Data may be processed with a delay, for example, in the device. Data may be processed externally from the device. For example, the data may be processed in a server, in a portable electronic device, and/or in a database that may perform the processing of the data.

Notifications may be delivered to the user, for example, in the form of an electronic mail message sent to a user-specified electronic mail address, push notifications, a text message sent via SMS (Short Message Service) to a user-specified mobile phone number, a calendar reminder set up by the system in a user-specified calendar, phone calls to a user-specified mobile or landline phone number, messages by a mobile phone application of a user's mobile phone, etc.

The time and/or duration of an animal's activity, consumption of calories (e.g., at a feeding area) and/or evacuation of food or liquid (e.g., at a waste area) may be recorded. For example, a date and/or time of the animal's trotting, the animal's visit to a waste area, and/or the animal's visit to a feeding area may be recorded. A time duration of the animal's presence inside the waste area may be recorded. The movements, orientations, and/or locations of the animal at a play area, feeding area, and/or a waste area may be recorded. All records may be stored and/or may be presented, for example, via a textual or graphical format.

Information relating to the animal may be accessed via a portable electronic device. The information may relate to a profile of the animal, motion data and/or signatures (e.g., signatures of activities) relating to the animal, activities of the animal, summaries relating to the activities, and the like, as described herein.

The portable electronic device may provide a user interface, for example, via an application downloaded on the portable electronic device. A user may create a profile associated with the animal. The application may display the animal's profile and/or may be facilitate the uploading of monitoring information of the animal. Icons or symbols displayed on the application may designate an animal activity that is being monitored and/or tracked. For example, a feeding bowl may be displayed to show feeding information, a litter box may be displayed to show defecation/urination information. Such data may be displayed in graph form for ease of reference.

Figure 6:
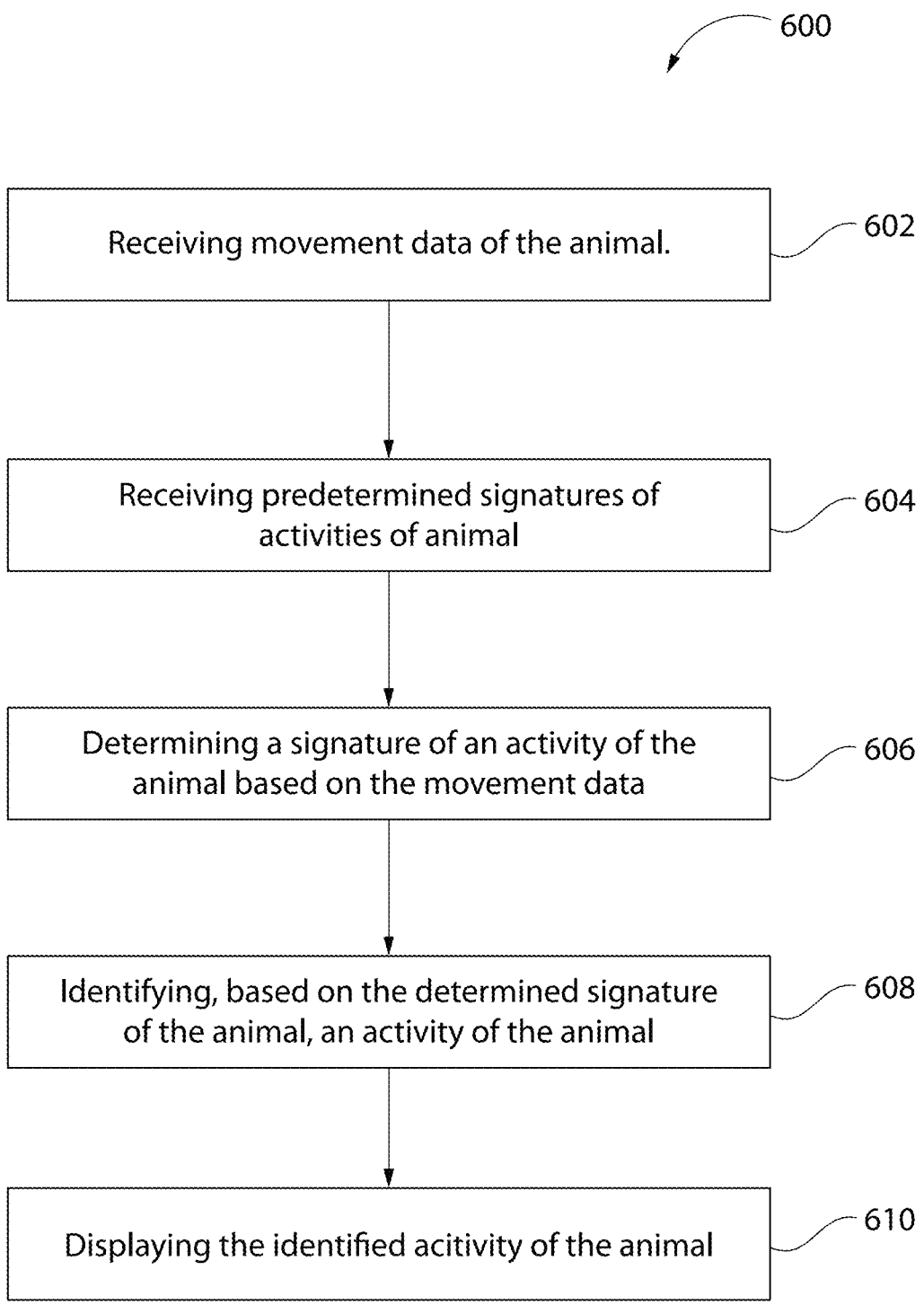
FIG. 6 is an example use of the system of FIG. 1, as described herein.

FIG. 6 describes an example method 600 of an animal monitoring and/or determining of an activity. At 602, data may be received. The data may be movement data that may be received from a sensor and/or from one or more other devices, such as a measuring device or one or more other devices. The data may be acceleration data, velocity data, location data, biometric data, and the like. The data may be received at a processor.

The data may be received and/or determined via a sensor (or other device) configured to detect a location of the animal, to detect the motion (or stillness) of the animal, to detect an orientation of the animal, etc. The sensor may be one or more of a variety of form factors, including, but not limited to, an accelerometer, a gyroscope, a magnetometer, weighing scales, weight transducers, force transducers, displacement transducers, pressure transducers, weight sensors, force sensors, displacement sensors, pressure sensors, load cells, photographic cameras, video cameras, camcorders, contact thermometers, non-contact thermometers, and a combination thereof. In addition, or alternatively, first sensor may be one or more of optical sensors, optical reflecting sensors, LED/photodiode pair optical sensors, LED/phototransistor pair optical sensors, laser diode/photodiode pair optical sensors, laser diode/phototransistor pair optical sensors, optocouplers, optical fiber coupled optical sensors, magnetic sensors, weight sensors, force sensors, displacement sensors, pressure sensors, various proximity sensors, such as inductive proximity sensors, magnetic proximity sensors, capacitive proximity sensors, and/or a combination thereof.

The sensor may include one or more photo electric sensors, such as a diffuse-reflective, through-beam, retro-reflective, and/or distance-settable sensor. For example, an area may be defined by a beam of light. When the beam of light is disrupted, it may be determined that the animal passed into the area or out of the area. The sensor may include a thermometer and/or a microphone that may be used to determine the presence or absence of an animal in an area. For example, urine and/or feces deposited by an animal within an area (e.g., a waste area) may change (e.g., increase) the temperature of the area or the temperature of the animal. Microphones may be used to determine the presence of the animal or activities of the animal (such as urination, defecating, or urination of the animals).

Data may be motion, location, orientation, etc., data of an animal. For example, the data may be tri-axial data (e.g., tri-axial acceleration data), as described herein. The data may correspond to a signature of an animal activity, such as a drinking signature, eating signature, urinating signature, defecating signature, scratching signature, turning (e.g., in circles) signature, crouching signature, sniffing signature, trotting signature, and the like. In examples a signature may correspond to one or more animal activities occurring at the same time, such as a signature corresponding to an animal performing a drinking activity and a scratching activity. In other examples each signature may represent a singular activity (e.g., a signature may only represent a signature of a urination activity).

At 604, predetermined data may be received. Predetermined data may be received from one or more other devices, such as a memory (e.g., a memory housed on a remote server). Predetermined data may be movement data (e.g., tri-axial acceleration data) previously collected, signature data previously collected, and the like.

At 606, the signature of the data (e.g., the data received from the sensor) may be determined (e.g., identified). The signature of the data may be determined based on the predetermined data previously collected. For example, a signature of previously collected tri-axial data may be identified as an animal drinking, eating, urinating, defecating, and the like. In such example, the values of the X, Y, and/or Z components of the animal's tri-axial acceleration data (e.g., tri-axial acceleration data received from the sensor) may be associated with previously collected tri-axial data identified as a signature of a drinking activity. The association of the acceleration data with the signature may be performed manually (via a user manually performing the association), automatically (via machine learning techniques, for example), or a combination of manually and automatically. The signature data of the animal may correspond to a singular activity of the animal (e.g., a defecation activity) or more than one activity of the animal. For example, signature data of the animal may correspond to a urination activity and a scratching activity.

At 608, an activity of the animal may be determined (e.g., identified) based on the determined signature. For example, the signature identified in 606 and associated with tri-axial acceleration data identified in 602 may be used to determine an activity of the animal, such as a urination of the animal. A single activity of the animal may be determined based on the determined signature and/or multiple activities may be determined based on one or more signatures. The signature and/or activity of the animal may relate to a period of time, such as a day, a time, and the like.

The data (e.g., motion data) relating to an activity (such as a urination activity) may be provided to a user, such as displayed to the user, as shown on FIGS. 4A and 4B. In such example the user may be notified that the animal has performed an activity (e.g., a urination activity) for a duration, for a certain amount of times, etc. The data may be provided to the user. The data may be used to determine a health condition of the animal. For example, the health condition of the animal may be based on the activity of the animal. The data may be used for behavior management and/or for training of the animal.

The health condition (e.g., illness, injury, disease, etc.) of the animal may be determined, for example, based on the animal activity (e.g., type of the animal activity, duration of the animal activity, number of occurrences of the animal activity, etc.). For example, a health condition of the animal may be based on the amount of times the animal eats, drinks, sleeps, urinates, defecates in a time period, the duration of the eating, sleeping, urination, defecation, etc. The time period may be an hour, a day, a week, a month, or the like. The health condition may be based on a number of times the animal activity occurs (e.g., within a predefined time period), a duration of the animal activity, or the like. For example, a healthy animal may be expected to drink, eat, sleep, urinate, and/or defecate a minimum and/or maximum amount of times during a time period. A mean and median of the above parameters may be defined for a healthy animal and/or for an unhealthy animal. If the animal performs a defined health parameter less than or more than an amount defined for a healthy animal, the animal may be identified as being unhealthy (e.g., a sick, injured, diseased, etc.).

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A method comprising:
    receiving, via a sensor, motion data of a first animal;
    receiving, from a memory, predetermined signatures of a second animal of one or more second animals, wherein the predetermined signatures of the second animal of the one or more second animals are associated with one or more activities of the second animal of the one or more second animals;
    determining, via one or more processors, a signature of an activity of the first animal based on the motion data of the first animal;
    identifying, based on the signature of the activity of the first animal and at least two of the predetermined signatures of the second animal, the activity of the first animal, wherein the at least two predetermined signatures of the second animal being at least one of: a predetermined signature of a successful urination posture and a predetermined signature of an unsuccessful urination posture, or a predetermined signature of a successful defecation posture and a predetermined signature of an unsuccessful defecation posture;

causing the identified activity of the first animal to be displayed via a display device, wherein each predetermined signature of the predetermined signatures is associated with a single activity of the second animal;

wherein the identified activity of the first animal comprises at least one of: a successful urination, an unsuccessful urination, a successful defecation, or an unsuccessful defecation; and wherein the signature of the activity of the first animal is at least one of: a successful urination posture, an unsuccessful urination posture, a successful defecation posture, or an unsuccessful defecation posture.

2. The method of claim 1 wherein the motion data of the first animal comprises the motion data in X, Y, and Z directions.

3. The method of claim 1 wherein the motion data of the first animal comprises at least one of an acceleration of the first animal, a velocity of the first animal, a location of the first animal, or a distance traveled by the first animal.

4. The method of claim 1 further comprising determining, via the one or more processors, a health condition of the first animal based on the identified activity of the first animal.

5. The method of claim 4 wherein the determination of the health condition of the first animal is based on a quantity of the identified activity of the first animal or a duration of the identified activity of the first animal.

6. The method of claim 1 wherein the first animal is a cat or a dog.

7. The method of claim 1 wherein the activity of the first animal is identified via machine learning techniques.

8. A system for determining an activity of an animal comprising:

a sensor configured to receive motion data of a first animal;

a memory configured to receive predetermined signatures of a second animal of one or more second animals, wherein the predetermined signatures of the second animal of the one or more second animals are associated with one or more activities of the second animal of the one or more second animals; and one or more processors configured to:

determine a signature of an activity of the first animal based on the motion data of the first animal;

identify, based on the signature of the activity of the first animal and at least two of the predetermined signatures of the second animal, the activity of the first animal, wherein the at least two predetermined signatures of the second animal being at least one of: a predetermined signature of a successful urination posture and a predetermined signature of an unsuccessful urination posture, or a predetermined signature of a successful defecation posture and a predetermined signature of an unsuccessful defecation posture; and cause the identified activity of the first animal to be displayed via a display device; wherein each predetermined signature of the predetermined signatures is associated with a single activity of the second animal; wherein the identified activity of the first animal comprises at least one of: a successful urination, an unsuccessful urination, a successful defecation, or an unsuccessful defecation; and wherein the signature of the activity of the first animal is at least one of: a successful urination posture, an unsuccessful urination posture, a successful defecation posture, or an unsuccessful defecation posture.

9. The system of claim 8 wherein the motion data of the first animal comprises the motion data in X, Y, and Z directions.

10. The system of claim 8 wherein the motion data of the first animal comprises at least one of an acceleration of the first animal, a velocity of the first animal, a location of the first animal, or a distance traveled by the first animal.

11. The system of claim 8 wherein the one or more processors are further configured to determine a health condition of the first animal based on the identified activity of the first animal.

12. The system of claim 11 wherein the determination of the health condition of the first animal is based on a quantity of the identified activity of the first animal or a duration of the identified activity of the first animal.

13. The system of claim 8 wherein the first animal is a cat or a dog.

14. The system of claim 8 wherein the activity of the first animal is identified via machine learning techniques.

* * * * *